United States Patent [19]

Revel et al.

[11] Patent Number: 4,889,803

[45] Date of Patent: Dec. 26, 1989

[54] PRODUCTION OF INTERFERON GAMMA

[75] Inventors: Michel Revel, Rehovot; Menachem Rubinstein, Givat-Shmuel; Yvez Mory, Rehovot, all of Israel

[73] Assignee: Yeda Research & Development Co., Ltd., Rehovot, Israel

[21] Appl. No.: 727,673

[22] Filed: Apr. 26, 1985

[30] Foreign Application Priority Data

Apr. 27, 1984 [IL] Israel ........................................ 71691

[51] Int. Cl.$^4$ .................. C12P 21/00; C12P 21/02; C12N 15/00; C12N 5/00; C12N 1/00
[52] U.S. Cl. .......................... 435/69.51; 435/240.2; 435/320; 435/172.3; 935/34
[58] Field of Search ................. 435/172.3, 68, 70, 240, 435/317, 240.2; 935/34

[56] References Cited

U.S. PATENT DOCUMENTS

| | | | |
|---|---|---|---|
| 4,405,712 | 9/1983 | Vande Wonde et al. | 435/70 |
| 4,656,134 | 4/1987 | Ringold et al. | 435/91 |
| 4,713,339 | 12/1987 | Levinson et al. | 435/91 |

OTHER PUBLICATIONS

Lai et al., PNAS U.S.A., vol. 77, pp. 244–248, Jan. 1980.
Berg et al., Mol. and Cell. Biol., vol. 3, pp. 1246–1254, Jul. 1983.
Kriegler et al., Mol. and Cell. Biol., vol. 3, pp. 325–339, Mar. 1983.
Scahill et al., PNAS, U.S.A., vol. 80, pp. 4654–4658, Aug. 1983.
Gray et al., Nature, vol. 298, pp. 859–863, Aug. 26, 1982.
Gillie et al., Cell, vol. 33, pp. 717–728, Jul. 1983.
Murai et al., Science, vol. 222, pp. 476–482, Nov. 4, 1983.
Kaufman et al., J. Mol. Biol., vol. 159, pp. 601–621 (1982).
Paul Bornstein et al., Regulatory Elements in the First Intron Contribute to Transcriptional, etc., Proc. Natl. Acad. Sci. U.S.A., vol. 84: 8869–8873 (Dec. 1987).
Neuberger and Williams, Nucleic Acids Res., 16: 6713–6722 (1988).
Lavett, J. Theor. Biol., 107: 1–36 (1984).
Lavett, Am. J. Hum. Genet., 36: 338–345 (1984).
Freytag et al., Molecular Strct. of the Human Arginosuccinate Synthetase Gene: Occurrence of Alternative mRNA Splicing, Mol. Cell. Biol., 4: 1978 (1984).
Luskey, Mol. Cell. Biol., 7: 1881–1983 (1987).
Peter Gruss, Mary Ann Liebert, Inc. Publ., Magic Enhancers?, 3: 1–5 (1984).
Sharp, The Harvey Lectures Series 81, Splicing of Messenger RNA Precursors, 81: 1–31 (1987).

*Primary Examiner*—Alvin E. Tanenholtz
*Attorney, Agent, or Firm*—Iver P. Cooper

[57] ABSTRACT

Interferon $\gamma$ is produced in highly purified form (activity exceeding $10^8$ units/ml-day) by CHO cells cotransformed by a first plasmid bearing the genomic human interferon gene under the control of the SV40 early promoter, and a second plasmid bearing a DHFR gene under similar control. Methotrexate selection yielded a clone which was a particularly efficient producer. Production of interferon $\gamma$ may also be facilitated by a Harvey sarcoma virus enhancer sequence.

15 Claims, 6 Drawing Sheets

CONSTRUCTION OF PLASMID pSVEγ121
(IFN-γ GENE UNDER CONTROL OF EARLY SV40 PROMOTER)

Cut with Hind III and Bcl I
Isolate large fragment
Fill in ends with DNA polymerase
Ligate with T₄ DNA polymerase Cut with BclI and Bam HI
Isolate 5.6kb fragment Cut with Bcl I
Dephosphorylate with calf alkaline phosphatase Ligate with T₄ DNA Ligase POLYACRYLAMIDE-SDS GEL ELECTROPHORESIS
OF Hu IFN-γ FROM CHO-γ 301 CELLS
PURIFIED ON MONOCLONAL ANTIBODY COLUMN

PRODUCTION OF INTERFERON GAMMA

RELATED APPLICATION

This application is related to Revel and Rubenstein, Israeli Appl. No. 71691, filed Apr. 27, 1984, and applicants claim the benefit of the filing date of that application for purposes of determining priority, pursuant to 35 USC 119.

FIELD OF THE INVENTION

The invention relates to a line of genetically engineered hamster cells that produce constitutively very large amounts of the human glycoprotein interferon-γ. Culture of these cells, designated CHO-γ 301, accumulate in the medium in which they are cultivated. This very large production is approximately 500 times higher than was previously obtained with human lymphocytes (Yip et al, Proc. Nat. Acad. Sci. USA, 79, 1820–1824, 1982) and 29 times that with engineered cells (Schaill et al, Proc. Nat. Acad. Sci. USA, 80, 4654–4658, 1983). By cultivating the CHO-γ301 cells, it is possible to produce every 24 hours 10 mg/l of culture of human IFN-γ which in then purified by affinity chromatography on columns of monoclonal antibodies, yielding a pure ($10^8$ units/mg) preparation of human IFN-γ.

BACKGROUND OF THE INVENTION

Interferons (IFNs) are a group of proteins produced by the cells of most vertebrates and characterized by their ability to inhibit the growth of virus cells exposed to these proteins.

Interferons are species specific, that is active mainly on cells from the same animal species from which they have been obtained. Thus human cells will be sensitive to human IFNs, but not to most animal IFNs. Human IFNs are classified in three groups: IFN α and β (also called type I IFNs) are produced by many cells of the body in response to viral inducers; in contrast, IFN-γ (also called type II IFN) is produced by certain T-lymphocytes in response to antigens or mitogens and its production is part of the immune response. IFN-γ differs from type I IFNs in its structure and in its functions. In particular, IFN-γ induces the synthesis of histocompatibility antigens (HLA class I and class II) which assemble on the surface cells and mediate the immune response of lymphocytes, at concentrations which are much lower than those needed to inhibit virus proliferation (Wallach et al, Nature 299, 833–836, 1982). This property of IFN-γ probably contributes in a most important way to the recognition and destruction of virus-infected cells, and of other modified cells such as cancer cells, by the immune system. It can be hoped therefore that IFN-γ will prove efficient in clinical trials to stimulate the immune system to destroy foci of viral infection and tumors.

A major obstacle to testing the clinical efficacy of IFN-γ is the small amount of IFN-γ. This was prepared from fresh human peripheral mononuclear cells stimulated by a combination of phorbol myristate and lectins. Such methods can yield only 10–20,000 units IFN-γ per ml of culture. Isolation of complementary DNA clones of the human IFN-γ mRNA sequence allowed one researcher to produce the protein in *E. coli* with much higher yields (Gray et al, Nature 295, 503–508, 1982). The bacterial IFN-γ differs, however, from the natural molecule by being unglycosylated and carrying 3–4 additional N-terminal amino acids.

However, the natural form of interferon gamma may be obtained from transformed mammalian cells. Haynes and Weissman, Nucleic Acids Res. 11: 687–706, (1983) constructed a plasmid bearing the dihydrofolate reductase (DHFR) gene under the control of the adenovirus major late promoter and a human gamma interferon cDNA gene under the control of the SV40 early promoter (derived from PKCR). Chinese hamster ovary (CHO) cells transformed by this plasmid expressed IFN-γ at a rate of 20,000–100,000 units.ml$^{-1}$.day$^{-1}$, in clones selected after exposure to 0.2 or 1.0 micromoles methotrexate. Unamplified CHO cells produced IFN-γ at a rate of 10–300 units.ml$^{-1}$.day$^{-1}$.

Scahill, et al., Proc Nat. Acad. Sci. USA, 80: 4654–58 (1983) cotransformed CHO cells with a first plasmid encoding the selectable marker DHFR and a second bearing a human gamma interferon cDNA gene under the control of the SV40 early promoter (derived from PSV2). CHO clones selected in methotrexate produced 50,000 units per ml. of culture medium.

Since the DHFR gene confers resistance to high concentratons of methotrexate, the cotransformed interferon gene is amplified by selection of transformed cells resistant to methotrexate, according to the method of Alt, et al., J. Biol. Chem., 253: 1357–70 (1978). See also, Bostock and Tyler-Smith, J. Mol. Biol., 153: 219–236 (1981); Nunberg, et al, PNAS (USA), 75: 5553–56 (1978).

The genomic human interferon gamma gene has been isolated and sequenced, and is thus known to include large intervening sequences (introns). Gray and Goeddel, Nature, 298: 859–863 (1982). Even though it is recognized that introns may be important in the formation of stable mRNAs, see Prochownik and Orkin, J. Biol. Chem, 259: 15386–15392 (Dec. 25, 1984), or may possess enhancer sequences, see Grilles, et al., Cell, 33: 717–728 (1983), interferon gamma cDNA has been utilized in the construction of eukaryotic interferon expression vectors. Goeddel and Gray, EP Appl. 77,670 (Apr. 27, 1983 publication).

While promoters are control elements which are effective only when positioned immediately 5' of the gene to be controlled, enhancers act relatively independently of their distance and orientation with respect to the coding region of the gene. Gruss, DNA 3: 1–5 (1984); Marx, Science, 221: 735–737 (Aug. 19, 1983). An enhancer region has been identified in the long terminal repeat (LTR) of the Harvey Murine Sarcoma virus. Kriegler ∂ Botchan, Mol. and Cell. Biol. 3: 325–339 (1983). Enhancer sequences may enhance the expression of heterologous genes, but their activity is believed to be host-specific and their mechanism of action is uncertain. Gruss, supra.

Berg, et al., Mol. and Cell. Biol., 3: 1246–54 (1983) have examined the effect of the SV40 72 bp repeat and the Murine Harvey Sarcoma virus 73 bp repeat enhancer sequences on the mouse beta globin promoter's control over the transcription of the *E. coli* galactokinase gene. They found that the Sv40 enhancer was stronger in CV-1 (primate) cells, while the reverse was true in L (mouse) cells. They also found that the effects of the two enhancers when present on the same DNA was additive. Luciw, et al., Cell, 33: 705–716 (1983) reported "provisional evidence that enhancer-promoter combinations functional in one set of experimental conditions may not work in another" (microinjection v.

transfection). Indeed, the findings of Emerman and Temin, Cell, 39: 459–467 (1984), suggest that an enhancer may inhibit expression of an exogenuous gene under some circumstances. Thus, success in enhancing expression of one exogenous does not guarantee success in expressing another.

SUMMARY OF THE INVENTION

In the present invention, we have been able to obtain CHO cell clones producing constitutively 1,000,000 units/ml per 24 HRS per 1,000,000 cells IFN-γ by using the human IFN-γ gene containing its large intervening sequences (introns) instead of the complementary DNA which is a copy of the processed IFN-γ mRNA. The presence of introns in the IFN-γ gene (Gray, Goeddel, Nature 298, 859–863, 1982) probably facilitates the processing and expression of IFN-γ mRNA transcribed from the transfected DNA. In addition, in our procedure, it was not necessary to link the DHFR DNA to the same vector which contains the IFN-γ gene but the two DNA vectors were simply mixed before transfection, greatly simplifying the construction of the DNA vectors. The fact that clones of CHO cells, producing 1 million units human IFN-γ per ml per 24 HRS and per million cells, could be obtained greatly facilitated the purification to homogeneity of the IFN-γ which was achieved by affinity chromatography on columns of monoclonal antibodies.

We have also been able to enhance expression of the interferon gamma gene by placement of the enhancer downstream from the SV40 Havey Murine Sarcoma virus promoter-DHFR cDNA unit.

Finally, high levels of purification of this interferon were achieved by adsorbtion to monoclonal antibody followed by alkaline elution.

One object of the invention is the constitutive production of IFN-γ at high rates from nonhuman cells.

Another object of the invention is the purification to homogeneity of IFN-γ.

Another object of the invention is the purification of the IFN-γ with minimal inactivation.

Another object of the invention is to provide an expression system for the production of IFN-γ.

Another object of the invention is to utilize a genomic IFN-γ gene to express IFN-γ in nonhuman cells.

Another object of the invention is to utilize a retroviral enhancer sequence, like the HSV sequence, to enhance transcription of an IFN-γ gene.

Another object of the inventions is to amplify a genomic IFN-γ gene by methotrexate selection of cells contransformed with a DHFR gene.

DESCRIPTION OF THE PREFERRED EMBODIMENTS

I. Isolations of human IFN-γ genomic clones

A human genomic library in lamda bacteriophage (Maniatis, et al., Cell 15, 687–701, 1978) was screened using two synthetic oligonucleotide probes γ1 (21 nucleotides complementary to codons 11 through 17) and γ3 (27 nucleotides complementary to codons 158 to the last 166th codon). The oligonucleotides were synthesized from the nucleotide sequence of the cDNA clone described by Gray et al (Nature 295, 503–508, 1982). One phage clone hybridizing to both oligonucleotides was selected by the procedure of Grunstein and Hogness (Proc. Natl. Acad. Sci. USA 72, 3961–3965, 1975) as modified by Mory et al (Eur. J. Biochem. 120, 197–202, 1981). This phage γ-6 was found to contain the entire IFN-γ gene and to be very similar to phage λ-10 of Gray and Goeddel (Nature 298, 859–863, 1982), but differed from it by having several different restriction sites in the 2 kb region preceding the gene.

II. Fusion of the human IFN-γ gene to the SV40 early gene promoter

Figure 1:
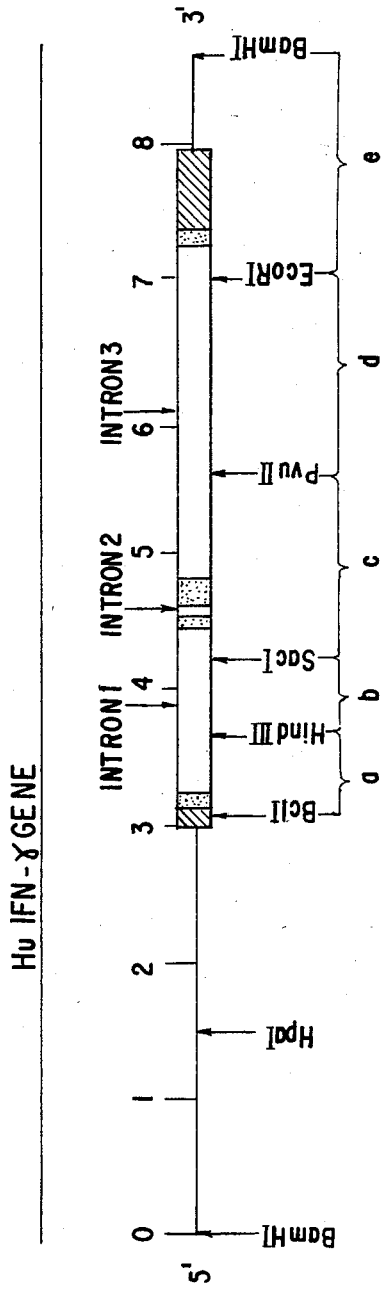
FIG. 1 shows the entire genomic IFN-γ gene isolated as a BamHl fragment.
Figure 2:
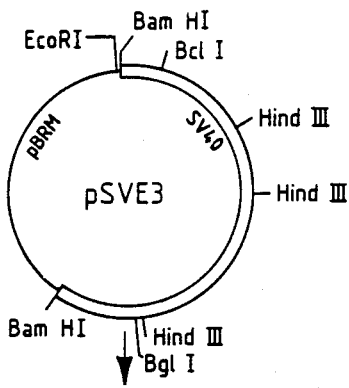
FIG. 2 shows the construction of pSVEγ121.
Figure 2:
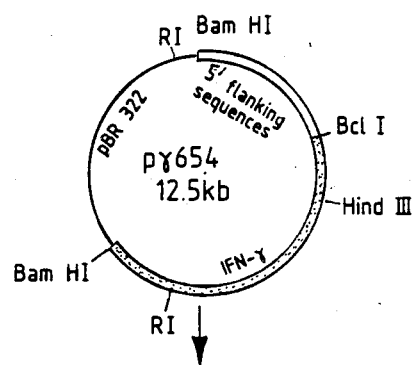
Figure 2:
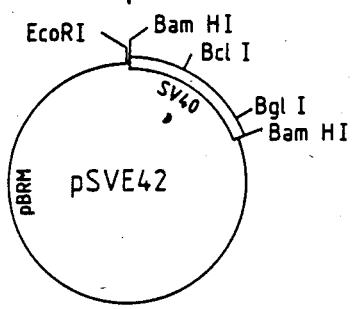
Figure 2:
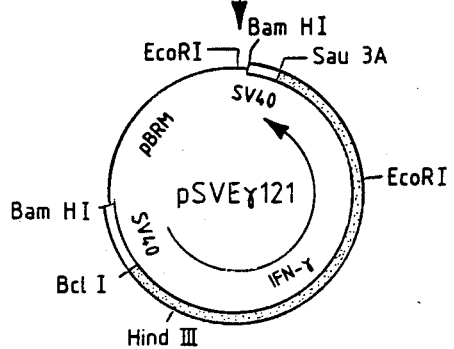

The entire IFN-γ gene with its three large introns, was excised from phage γ-6 DNA as a BamH1 fragment (FIG. 1) of 8.6 kb and subcloned in pBR 322 to yield plasmid pγ654 (FIG. 2). A unique $Bcl_1$ restriction site located in the 5′-untranslated region 60 bp upstream from the initiator ATG codon (FIG. 1) was used to cleave pγ654. After recutting with BamH1, the 5.6 kb fragment containing the IFN-γ gene was isolated and introduced into the expression vector pSVE 42 (FIG. 2). This vector, derived from pSVE3 (Hartman et al., Proc. Natl. Acad. Sci. USA 79, 233–237, 1982) contains the origin of SV40 replication and the promoter of the T-antigen gene. The $Bcl_1$ site of IFN-γ was fused to the filled-in $Hind_{III}$ site of SV40 which is located 60 bp downstream from the SV40 early mRNA start site, creating a chimeric transcription unit in which the ATG codon of IFN-γ is now 120 bp downstream from the RNA start site. The resulting plasmid was cloned in E. coli MM294 and called pSVEγ121.

III. Transfection of hamster CHO cells by the human IFN-γ gene

Figure 3:
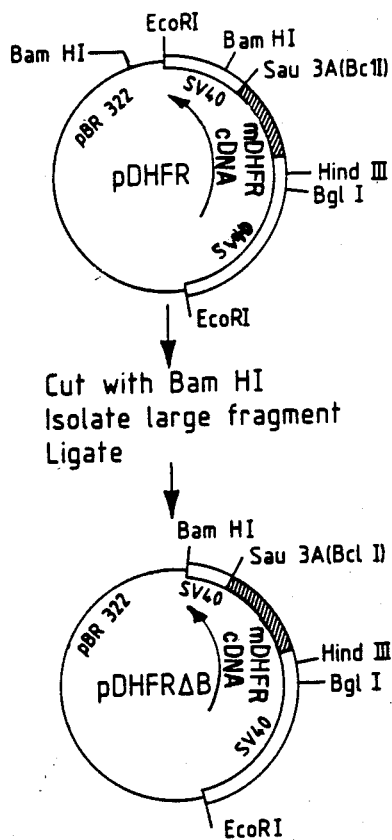
FIG. 3 shows the construction of pDHFRΔβ.

A dihydrofolate reductase deficient mutant (DNFR) of hamster CHo-K1 cells (clong DXB11) (Urlaub and Chasis, Proc. Natl. Acad. Sci. USS 77, 4216–4220, 1980) was used for DNA-mediated co-transformation (Wigler et al., Cell 16, 777–785, 1979). As selective marker, we used plasmid DNA pDHFR Δβ derived from pSVDFR (FIG. 3), which contains the mouse DHFR cDNA fused to the SV40 early gene promoter and to a splicing region of mouse IgG γ2a (Horowitz M. and Sharp P. personal communication). About $0.5 \times 10^6$ CHO DHFR-cells were exposed to a $CaPO_4$-DNA coprecipitate prepared by mixing 20 μg of pSVEY121 DNA with 5 μg pDHFR Δβ DNA in 0.45 ml of 0.1 mM Tris-HCl pH 7.9 0.1 mM EDTA with 0.5 ml of 280 mM NaCl, 1.5 mM $Na_2HPO_4$, 50 mM HEPES buffer pH 7.1, before adding 0.05 ml of 2.5M $CaCl_2$ with gentle shaking and allowing precipitation for 30 minutes. The cells were left with the precipitate for 30 minutes at room temperature, then 9 ml of Nutrient mixture F-12 (Gibco Company) and 10% fetal calf serum(FCS) were added and the cells incubated at 37° C., in 5% $CO_2$, for 4 hours. The medium was removed and the cells were osmotically shocked with 10 percent glycerol in F-12 for 4 minutes, then washed and incubated 48 hours with F-12, 10 percent FCS. Cells were then trypsinized and subcultured 1:4 into selective medium composed of Dulbecco's modified Minimum Essential Medium (DMEM), 150 μg/ml proline and 10 percent FCS which had been extensively dialyzed against phosphate buffered saline to remove free nucleosides. Only cells capable of de novo purine biosynthesis, and hence DHFR+, can grow in this selective medium and form colonies. Medium was changed every 3–4 days and clones were isolated after 10–12 days.

Eight such DHFR+ clones were picked up by mild trypsinization in small cylinders grown to mass cultures and tested for the secretion of human IFN-γ. The cells were grown in 9 cm diameter plastic dishes with 10 ml medium to a total of about $4 \times 10^6$ cells. Medium was changed every 24 hours and the amount of IFN-γ in the medium was assayed by two methods: (1) inhibition of the cytopathic effect of Vesicular Stomatitis virus on culture of human amniotic cells WISH exposed overnight to various dilutions of IFN-γ, and (2) a double monoclonal antibody radiometric assay for human IFN-γ. Both methods are described by Novick et al (EMBO J. 2, 1527–1530, 1983). We found that 2 out of the 8 clones produced 6000–8000 units IFN-γ-ml-24 hours of IFN-γ and 1 clone produced a few hundreds units/ml. The highest producer cell clone CHO-γ12 was selected for amplification.

IV. High Production of human IFN-γ after amplification of the human IFN-γ gene in CHO cells Different cultures of CHO-γ12 cells were exposed to either 20 or 50 nmoles Methotrexate (Mx), which causes the death of most cells but allows us to select for resistant clones of cells in which the DNA segment containing the DHRF cDNA has been amplified and is now present in multiple copies. The co-transfected human DNA segment containing the IFN-γ gene is in most cases co-amplified by this procedure, as can be demonstrated by Southern blots of the cellular DNA. A dozen Mx-resistant clones were tested as above for secretion of human IFN-γ. Two clones (CHO γ146, γ148) resistant to 20 nM Mx, produced 190,000 units/ml/24 hours and three clones (γ133, γ135, γ155) resistant to 50 nM mx produced 290,000 units/ml/24 hours. Four of these cultures were then reexposed to 300 nM Mx and from each a resistant culture (γ301, γ302, γ303, γ304), producing 800,000 units/ml/24 hours, was obtained (Table 1.) In 9 cm dishes containing approximately $6 \times 10^6$ cells in 10 ml medium the amount of IFN-γ produced was about 1 million units per million cells, the IFN-γ accumulating at a rather constant rate during the 24 hours. The specific activity of natural human IFN-γ was estimated to be between $5 \times 10^7$ and $10^8$ units/mg protein (Novick et al., EMBO J. 2, 1527–1530, 1983). The CHO-γ 301 culture produces, therefore 10–20 μg IFN/$10^6$ cells/day, and excretes it into the medium.

Figure 4:
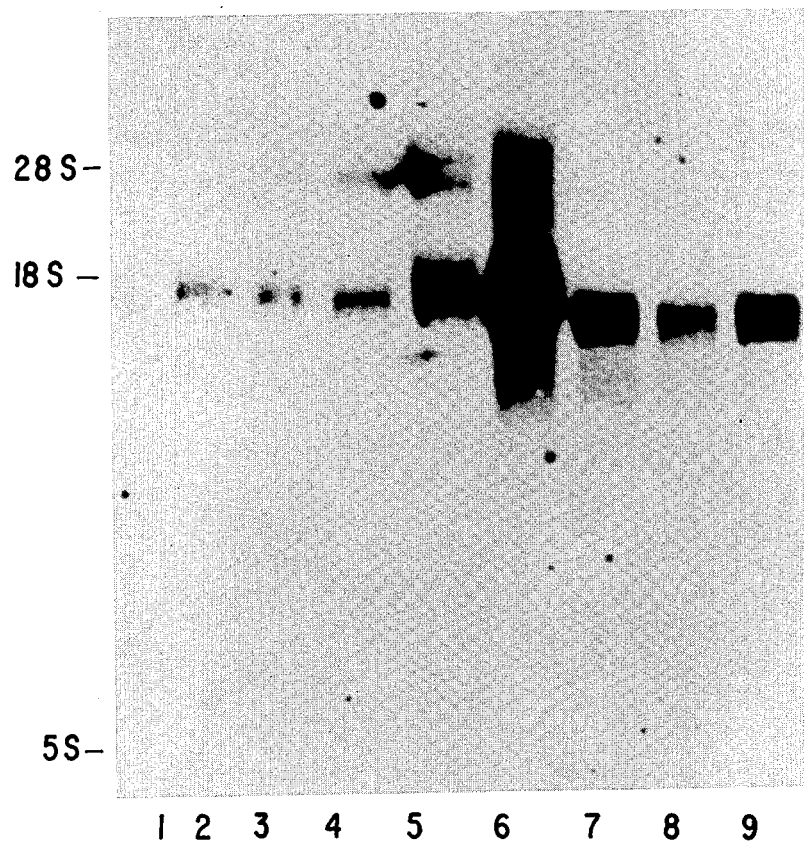
FIG. 4 shows a Northern blot analysis of total call RNA for Hu IFN-γ mRNA sequences in CHO-γ cell lines.

The production of human IFN-γ in the present CHO-γ 301 cell line is very high as compared to other cell culture systems. Using peripheral blood mononuclear cells, stimulated by phorbol myristate acetate and phytohaemagglutinin, Yip et al., (Proc. Natl. Acad. Sci USA 78, 1601–1605, 1981) obtained up to 5,000 units/ml/$6 \times 10^6$ cells in 24 hours and up to 20,000 units/$6 \times 10^6$ cells after 90 hours. The CHO-γ 301 cells produce 500 times more human IFN-γ and do not require stimulation, allowing the continuous harvest of the IFN. The production level in the present CHO-γ 301 cells is also 20 times higher than that obtained in CHO cells transfected by human IFN-γ complementary cDNA (Scahill et al., Proc. Natl. Acad. Sci. USA 80, 4654–4658, 1983; Haynes and Weissman, Nucleic Acids Res. 11, 687–706, 1983). We attribute this difference to the fact that the introns present in our construction, facilitate the expression of the transfected and amplified human gene. This was demonstrated by the analysis of total cellular RNA from CHO-γ 301 cells for the presence of IFN-γ mRNA by hybridization to IFN-γ DNA, (FIG. 4). These cells contain a very high level of IFN-γ specific mRNA which is at least 50 times higher than what is found in the non-amplified CHO-γ12 cells.

V. One-step derivation of high IFN-γ producer cells

Figure 5:
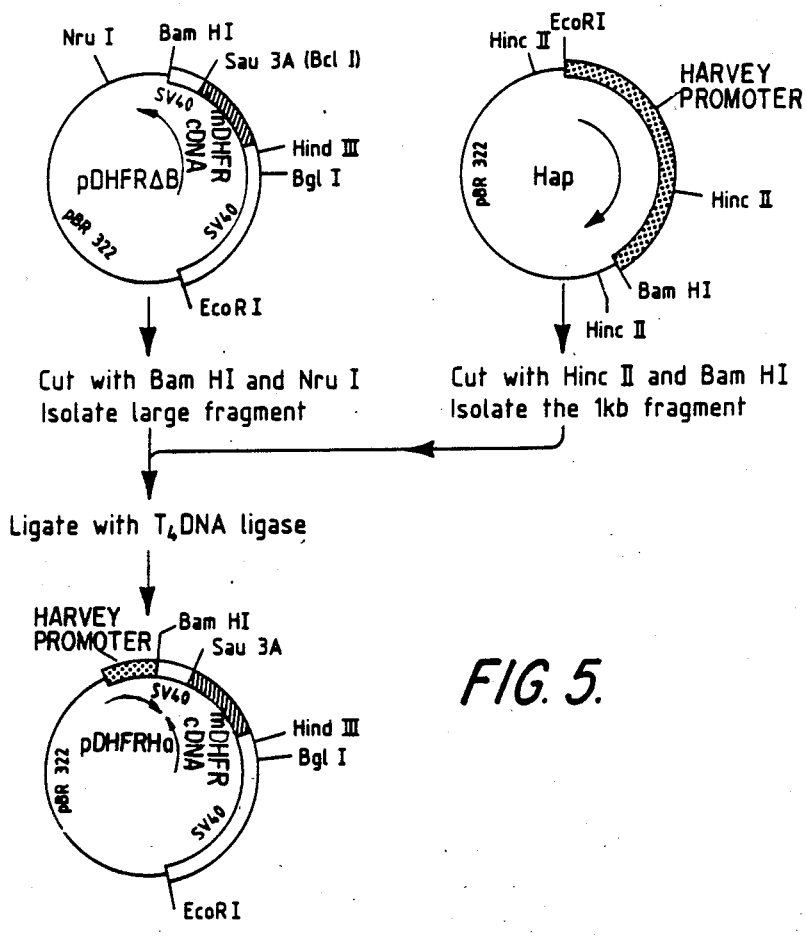
FIG. 5 shows the construction of pDHFRHa.

Expression of genes can be greatly increased by the presence of "transcriptional enhancer" DNA sequences (Gruss, DNA 3, 1–5, 1984). The SV40 early gene promoter contains a 72 bp repeat which serves as an enhancer, but expression from this promoter can be further increased by adding retrovirus LTR regions which contain a strong enhancer (Kriegler and Botchan, Mol. Cell. Biol. 3, 325–339, 1983). We have constructed an improved pSVDHFR plasmid DNA to be used for co-transfection with the human IFN-γ gene pSVEY121, which yields in one step (without amplification) very high levels of IFN-γ. The improved pSVDHFR vector (pDHFR Ha) was constructed by inserting a $Hinc_2$-BamH1 fragment of the Harvey murine sarcoma virus downstream to the fused SV40 promoter-DHFR cDNA, and in the opposite orientation (FIG. 5). Co-transfection of CHO-DHFR cells with pSVEγ121 and pDHFR-Ha DNA gave us 3 clones CHFR+, one of which γ21, expressed IFN-γ constitutively at levels of 150,000 units/ml/day, i.e. 10 times more than the other unamplified transformant cells. Analysis of the RNA from CHO-γ21 cells showed a very strong band of IFN-γ mRNA (FIG. 4), confirming the stimulatory influence of the Harvey virus enhancer on expression of the neighboring genes. These very high levels were obtained in one step after transfection, that is without amplification. When we applied Mx to CHO-γ_21 cells, a further amplification could be obtained and yields of 400,000 units/ml/day were achieved.

VI. Industrial production of human IFN-γ from CHO-γ 301 cells

To obtain maximal yields of human IFN-γ, the CHO-γ 301 cells are preferably grown to high density on suitable glass, plastic or other polymeric surfaces (microcarriers) and maintained in the cultures with daily changes of the medium. The culture medium (DMEM with 150 μg/ml proline) should contain a minimum of foreign proteins. We have found that 1 percent FCS in the medium is sufficient to give optimal yields of IFN. Stationary cultures in large tissue culture plastic trays, give the best yields of IFN-γ. Each tray with 50–100 ml of medium yields 100 million units of IFN-γ every 24 hours. An industrial production unit of 50 trays (500 cm² each) gives 50 mg IFN-γ daily. Each tray with 50–100 ml of medium yields 100 million units of IFN-γ every 24 hours. An industrial production unit of trays (500 cm² each) gives 50 mg IFN-γ daily. This represents a very important advance over existing methods for producing this precious and sparse material. In addition, and most important, the material produced is identical to the natural IFN-γ produced by human blood cells, which is not the case for the product made from *E. coli* which is unglycosylated and differs at its N-terminal end from the natural IFN-γ. Evidence for the identity of CHO-IFN-γ produced by the present methodology with the natural human glycoprotein was obtained by purification on columns of monoclonal antibodies.

VII. Purification of IFN-γ from CHO-γ 301 cells

Five liters of medium from CHO-γ 301 cultures were concentrated by ultrafiltration on a Pellicon membrane (Millipore Co.) with a cutoff of 10,000-Mr. The concentrated solution (245 ml) was centrifuged at 10,000xg for 10 minutes at 4° C. and applied with a flow-rate of 0.5 ml/min to a column of monoclonal antibody number 3—3 bound to polyacryl hydrazide-agarose (10 ml agarose, 9 mg/ml IgG). The column (at 4° C.) was washed with phosphate-buffered saline (400 ml), followed by 1M NaCl at pH 7 (400 ml). IFN-γ was then eluted from the column with 3M NaCl, 0.15M NH4OH pH 10.5–11.0 and 6 fractions of 10 ml each were collected and immediately neutralized with 0.4 ml of acetic acetic acid 1N for each fraction. The purification was over 3,000 fold with no loss of activity. The specific activity of the purified IFN-γ reached $1.6 \times 10^8$ units/mg protein (Table 2).

Figure 6:
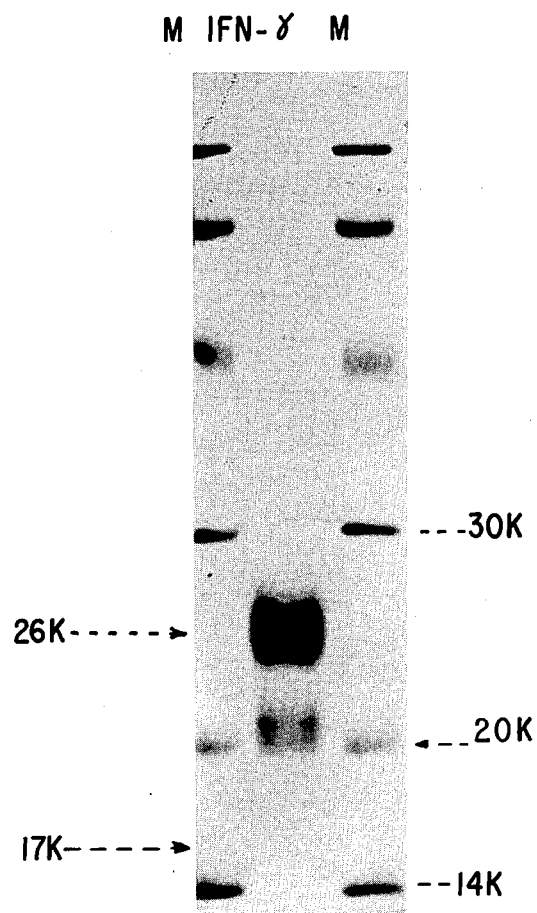
FIG. 6 shows the result of polyacrylmaide-SDS gel electrophoresis of Hu IFN-γ from CHO-γ-301 cells purified on a monoclonal antibody column.

Analysis of the eluted proteins by sodium dodecyl sulfatepolyacrylamide gel (15 percent) (FIG. 6) electrophoresis revealed a major protein band at 26,000 Mw, which co-migrates with the main component of natural IFN-γ extracted from blood cells. An additional 21,000 Mw band represents a partially glycosylated form of IFN-γ (Novick et al, EMBO J. 2, 1527–1530, 1983: Yip et al, Proc. Natl Acad. Sci. USA 79, 1820–1824, 1982). A very small amount of a 17,000 Mw protein is also present and corresponds to the size of non-glycosylated IFN-γ as shown by comparison to the non-glycosylated bacterially produced human IFN-γ (Gray et al, Nature 295, 503–508, 1982).

The procedure herein described is therefore applicable to the industrial production of pure human IFN-γ at low costs and with a minimum of manipulations. Large batches of IFN-γ can be purified in one step yielding 50 million units per ml of column. Large columns of 1–300 ml can be easily prepared for industrial use. The same column can be used for repeated uses for prolonged periods of time.

The novel process for the production of human IFN-γ in pure form is based on several inventive steps which represent significant progress over previously described methods, using either blood cells, or bacteria, or hamster cells subjected to genetic engineering. The most significant progress is in the amounts of IFN-γ obtained by the cell line designated CHO-γ 301. Yields are 20 times higher than those obtained by other authors (Scahill et al, Haynes and Weissmann, loci cited) in hamster cells. This difference stems in part from our use of a large genomic DNA segment containing the natural introns of the IFN-γ gene instead of the cDNA segment, which is only a copy of the mRNA. The difference also stems from optimization of the amplification and cell growth conditions. Yields are similar to what could be obtained in bacteria, but with the significant advantage that the product of hamster cells is glycosylated identically to the human product. Finally, yields are 100–500 times higher than with human blood cells and the need for induction is eliminated. The purification procedure on monoclonal antibodies using ammonia for elution represents a significant inventive step since IFN-γ is destroyed by acid elution, which was used for affinity chromatography until now. The procedure has allowed us to determine th N-terminal sequence of mature IFN-γ. Also novel invention is the use of the Harvey sarcoma virus enhancer (section V) to enhance expression of IFN-γ.

TABLE 1

PRODUCTION OF HUMAN IFN—γ BY CLONES OF HAMSTER CHO CELLS

| Transfected Plasmid DNAs | DHFR+ clone | Clones Resistant to Methotrexate | | |
|---|---|---|---|---|
| | | 20 nM | 50 nM | 300 nM |
| pSVEγ121 pDHFR Δβ | γ-12 8,000 U/ml | γ-146 192,000 U/ml | γ-133 280,000 U/ml | γ303 800,000 U/ml |
| | | | | γ-301 800,000 U/ml |
| | | | γ-135 290,000 U/ml | γ302 800,000 U/ml |
| | | | γ-155 260,000 U/ml | γ-304 800,000 U/ml |
| pSVEγ121 pDHFR—Ha | γ-21 150,000 U/ml | | | γ-200 400,000 U/ml |

Cultures contained $0.6 \times 10^6$ per ml

TABLE 2

AFFINITY PURIFICATION OF IFN—γ ON MONOCLONAL ANTIBODY COLUMN

| Fraction | Volume ml | Protein mg | Units ($10^6$) | Specific Activity units/mg | Purification Factor Fold | Purification Yield Percent |
|---|---|---|---|---|---|---|
| Crude Concentrate (load) | 5,000 | 1,530 | 750 | $5 \times 10^4$ | | |
| | 245 | 1,530 | 750 | $5 \times 10^4$ | 1 | 100 |
| Unbound + wash 15 | 1,045 | | 290 | | | |
| Eluate | 30 | 2.5 | 410 | $1.6 \times 10^8$ | 3,200 | 54 (89*) |

*Yield calculated as total activity recovered, minus unbound. Yields were determined by bioassay and (in parantheses) by RIA.

The preferred cell line, CHO-γ 301, was deposited on June 13, 1984, with the Institut Pasteur, an International Depository Authority under the Budapest Treaty, as I-310.

While we have described the use of an IFN-γ gene which is wholly genomic in origin, it may be possible to achieve comparable levels of expression by utilizing a "mini-gene", i.e., one only partially genomic in origin, by retaining only the introns found to have a stabilizing or enhancing effect. Additionally, it is possible to utilize a synthetic equivalent of the genomic sequence, with or without changes in codon usage.

While we have described the use of a particular DHFR cDNA gene, other genes capable of conferring methotrexate resistance on the host cell may be employed.

In addition to the natural Harvey Marine Sarcoma virus enhancer, we envision that modified sequences which retain enhancer activity may find utility in the practice of this invention.

We claim:

1. A method of producing human gamma interferon which comprises (a) providing Chinese hamster ovary cells bearing a first DNA sequence which codes on expression for human gamma interferon and includes at least one intron of the genomic human gamma interferon gene, said first DNA sequence being operably linked to a constitutive promoter functional in such cells, said promoter being a non-interferon promoter, said cells also bearing a gene coding on expression for dihydrofolate reductase, said gene likewise being operably linked to a constitutive promoter functional in such cells; (b) cultivating the cells in a medium containing methotrexate at a level toxic to cells which do not constitutively express dihydrofolate reductase, whereby the DHFR gene and the gamma interferon gene are co-amplified, and (c) cultivating such cells under conditions in which the cells constitutively express human gamma interferon in recoverable quantities.

2. The method of claim 1 wherein the first DNA sequence comprises the entire sequence of the genomic human gamma interferon gene.

3. The method of claim 2 wherein such cells produce human gamma interferon at a rate of at least about 190,000 units/ml-day.

4. The method of claim 2 wherein such cells produce human gamma interferon at a rate of at least about 260,000 units/ml-day.

5. The method of claim 2 wherein such cells produce human gamma interferon at a rate of at least about 800,000 units/ml-day.

6. The method of claim 2 wherein the cells are resistant to at least about 20 nM methotrexate and the DHFR and gamma interferon genes are co-amplified with at least about 20 nM methoxtrexate.

7. The method of claim 2 wherein the cells are resistant to at least about 50 nM methotrexate and the DHFR and gamma interferon genes are co-amplified with at least about 50 nM methotrexate.

8. The method of claim 2 wherein the cells are resistant to at least about 300 mM methotrexate and the DHFR and gamma interferon genes are co-amplified with at least about 300 nM methotrexate.

9. The method of claim 2 wherein after amplification with methotrexate, such cells contain at least about 50 times more human gamma interferon-specific mRNA than such cells contained prior to amplification.

10. The method of claim 2 wherein the constitutive promoter operably linked to the first DNA sequence is the SV40 early promoter or a derivative thereof which includes the 72 base pair repeat of the SV40 early promoter.

11. The method of claim 10, wherein the Harvey murine sarcoma virus enhancer sequence is operably associated with said first DNA sequence and enhances expression of the human gamma interferon encoded by that sequence.

12. Recombinant DNA molecules having the identifying characteristics of the vector pSVEgamma121.

13. Chinese hamster ovary cells cotransformed with pSVEgamma121 and a plasmid conferring a DHFR+ phenotype.

14. The method of claim 1 wherein the cells bear the plasmid pSVEgamma121.

15. The method of claim 2 wherein cells bearing the plasmid pSVEgamma121 are cultivated in step (b) in a medium containing at least 300 nM methotrexate, and the cells produce interferon gamma at a rate of at least about 400,000 units/ml-day.

* * * * *